United States Patent [19]

Stoy

[11] Patent Number: 5,624,727
[45] Date of Patent: Apr. 29, 1997

[54] STRUCTURAL DEVICES WITH CHANGING MECHANICAL PROPERTIES RESPONSIVE TO EXTERNAL FORCES

[75] Inventor: Vladimir A. Stoy, Borough of Princeton, N.J.

[73] Assignee: S.K.Y. Polymers, Inc., Rocky Hill, N.J.

[21] Appl. No.: 355,657

[22] Filed: Dec. 14, 1994

[51] Int. Cl.$^6$ ............................................. B32B 9/00
[52] U.S. Cl. ............................ 428/76; 428/68; 428/69; 428/72; 428/913; 602/3; 602/75; 607/96; 607/104
[58] Field of Search ........................... 428/68, 69, 72, 428/76, 913; 602/3, 75; 607/96, 104

[56] References Cited

U.S. PATENT DOCUMENTS 5,405,671  4/1995  Kamin .......................... 428/76

*Primary Examiner*—Nasser Ahmad
*Attorney, Agent, or Firm*—Kenneth P. Glynn, Esq.

[57] ABSTRACT

This application describes devices which have a first softer formable state, and the second stiffer shape-retaining shape and which are capable of repeatable transition from the first state to the second state (or vice versa) on demand. The device comprises:

(a) a hollow body having at least partial flexibility and being capable of containing a plurality of particular material therein;

(b) a plurality of particular material permanently located within said hollow body;

(c) a fluid medium in the hollow body and intermixed with the particulate material when the device is in its first state, and removed at least partly from the hollow body and the particulate material when the device is in its second state;

(d) fluid transfer means for removing the fluid medium from the hollow body and the particulate material or to return the fluid medium thereto in a predetermined manner, thereby being adapted to transform the device from the first state to the second state and vice versa; and, (e) a fluid medium receptor located within said hollow body and connected to said fluid transfer means. As the fluid medium is transferred out of the hollow body, the individual elements of the particulate material are becoming capable of mutual interaction and the device gets into its second, shape-retaining shape. p1 As a rule, the fluid medium can be transferred into (or from) a fluid medium receiver. The receiver is advantageously located within the hollow body.

41 Claims, 4 Drawing Sheets

FIRST STATE (RIGID):

FIG. 5A

SECOND STATE (FORMABLE):

FIG. 5B

FIRST STATE (FORMABLE):

FIG. 6A

SECOND STATE (RIGID):

FIG. 6B $T < T_S$
$T > T_S$

STRUCTURAL DEVICES WITH CHANGING MECHANICAL PROPERTIES RESPONSIVE TO EXTERNAL FORCES

BACKGROUND OF THE INVENTION

1. Field of the Invention

The present invention relates to devices with variable stiffness, and more specifically to such devices which have a first state which is plastically deformable or flexible or at least semi-flexible, and a second state which is less deformable or flexible than the first state. Such devices have diverse applications, e.g., for items which should be flexible for shaping, inserting, removing, opening, closing, and other physical movement, but which should be less flexible or even rigid when movement is completed and some rigidity is required. These devices may include medical devices, e.g., casts, implants, surgical devices, physiological control devices, etc.; footwear, e.g., shoes, sneakers, ski boots; headwear and sportswear, such as shoulder pads, helmet padding; furniture, e.g., seats, beds of selected firmness, shapable chairs; protective structures for goods, e.g., shaping a package to an odd shaped device; as well as other engineering and special application products.

2. Information Disclosure Statement

There have been numerous devices developed over the years which have two states, one flexible, the other rigid, and the principle of having a flexible, deformable or flowable material set in place is well known. Thus, there are plasters, amalgams, spackle, concrete, plastics, blow foams and other materials that enable a user to first shape and then set a material for custom or specialty results. However, few are capable of increased rigidity on demand, and rely-upon their own physical characteristics, e.g., drying time, polymerization or reaction time, etc. These may be slowed or sped up but cannot usually be activated on demand without the need to add a catalyst, heat, air or the like.

Further, these are even fewer devices available or known which have a formable state and a rigid state and these states are repeatable at will, e.g., the device may be cyclable back and forth between the two states. Inflatables are one exception and liquid fillable devices are another, e.g., a waterbed is readily deformable unfilled and more rigid filled. However, the inflation by water or other fluids has severe limitations due to the inherent fluid properties.

Moreover, inflation increases the device volume and the content of the pressurized medium can be inconvenient or even hazardous in some situations.

Some systems which could change its mechanical properties "on demand" can be useful in many practical applications. Since the change is due to an interaction of the material with an external impulse, they may be referred to as "interactive materials" for short.

They are a sub-class of so called "smart materials" or "smart systems" which are capable of changing their properties in general (optical, electrical, mechanical, magnetic, etc.) in response to an impulse. The "smart materials" include devices such as non-linear optical, opto-electric and piezo-electric materials. From the systems changing their mechanical properties, well-known interactive materials are the "electro-rheological fluids" which increase their viscosity (or even solidify) if placed in an external electric field. They can be used in clutches and transmissions; in hydraulic systems; in "smart structures" damping mechanical vibrations or reacting on an external stress; and are contemplated for many other uses. They have several limitations. The "solid state" is actually a rather soft gel with a relatively low yield stress. This makes them suitable only for a limited number of applications. Second, the electric field intensity required is rather high (around kV per millimeter or more). Third, some of the fluids require a certain narrow temperature range for their optimum function.

In the spite of these limitations, the systems based on the electro-rheological fluids attracted considerable interest in recent years.

Another type of known interactive system with changing properties "on demand" are so called memory materials (which are both polymers or metals). They change mechanical properties if heated over a certain temperature, and return from their "deformed" to their "inherent" shape. These systems have several inherent limitations. The change of state is triggered by reaching a certain pre-set temperature only; and the change of state (or shape) is irreversible. In spite of these limitations, these materials have numerous uses: intraocular lenses for small incision; spectacle frames; safety valves; safety switches; surgical instruments; micro-alignment devices fiber-optic splices; connectors; clamps; fasteners and many other uses.

Still another type of materials changing mechanical properties in response to the environmental changes are hydrogels. Dry, rigid "xerogels" can swell in water and change into soft, elastic hydrogels. The main limitation is the obvious dependence on the presence of water. Another limitation for some applications is the change of mass and size due to the swelling. Still another limitation is the rather lengthy and "one-way" swelling process. In spite of these limitations, hydrogels have found number of applications using this change of properties in the presence of water: seals, dilators, sensors, surgical devices insertable into body cavities (e.g., catheters) etc.

The present invention, on the other hand, relies upon an opposite mechanism, e.g., the removal of fluid to impart rigidity, and the inclusion of fluid to enhance flexibility or formability. Thus, notwithstanding the existence of flexible rigid devices, none show or suggest the present invention device using the aforesaid mechanism.

SUMMARY OF THE INVENTION

This application describes devices which have a first softer formable state, and the second stiffer shape-retaining shape and which are capable of repeatable transition from the first state to the second state (or vice versa) on demand. The device comprises:

(a) a hollow body having at least partial flexibility and being capable of containing a plurality of particular material therein;

(b) a plurality of particular material permanently located within said hollow body;

(c) a fluid medium in said hollow body and intermixed with said particulate material when said device is in its first state, and removed at least partly from said hollow body and said particulate material when the device is in its second state;

(d) fluid transfer means for removing the said fluid medium from said hollow body and said particulate material or to return said fluid medium thereto in a predetermined manner, thereby being adapted to transform said device from the first state to said second state and vice versa; and, (e) a fluid medium receptor located within said hollow body and connected to said fluid transfer means. As the said fluid medium is transferred out of the said hollow body, the individual elements of the said particulate material are becoming capable of mutual interaction and the device gets into its second, shape-retaining shape.

BRIEF DESCRIPTION OF THE DRAWINGS

The present invention is more fully understood when the specification is taken in conjunction with the drawings appended hereto, wherein.

DETAILED DESCRIPTION OF THE PRESENT INVENTION

There is a continuing search for new "interactive systems" which would provide new capabilities and which would remove some of the limitations of the current types.

This application discloses a new type of the interactive device, namely, a solid body which reversible changes its stiffness on demand in response of a suitable external impulse.

Such a device can change from a readily deformable, soft state into a more rigid and shape-retaining consistency.

The working principle behind this action is a fluid medium redistribution which affects the mutual interaction between a multitude of solid bodies or particles within the device. This change can be accomplished by various impulses causing the fluid redistribution within the system. The possible impulses include positive or negative pressure change; temperature change; application of electric and/or magnetic field; or exposure to light.

Preferably, the stiffness change can be achieved without a substantial change of the weight or of the volume of the device.

Figure 1:
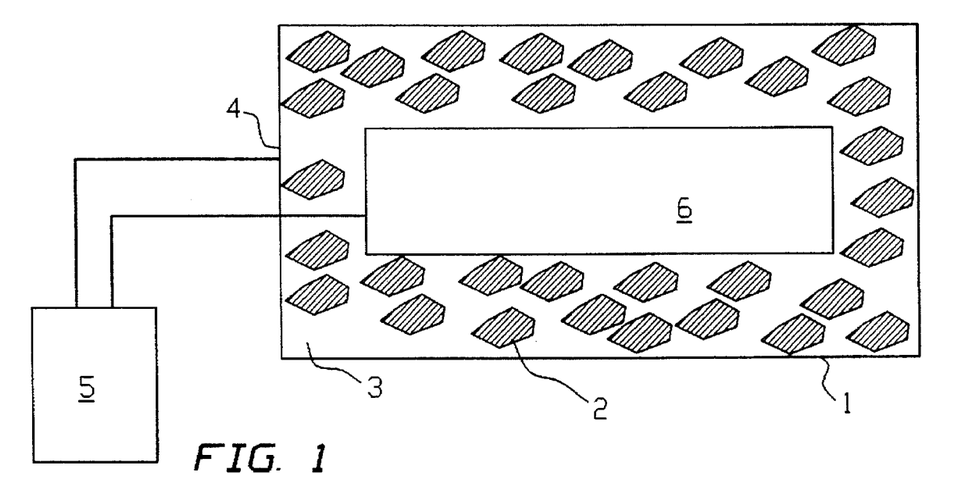
FIG. 1 illustrates a block diagram of the present invention device.

The present invention device is schematically depicted by the block diagram in FIG. 1. It comprises a hollow body which has a substantially deformable wall 1, containing and encasing the following:

a) multiple solid elements or particles, such as particle 2;

b) a fluid medium 3;

c) a fluid medium receiver 6 capable of containing the excess of the fluid; and, d) a mechanism capable of removing the fluid from the interstitial spaces between the solid particles and to transfer it back on demand, represented by the fluid transfer device 5 and the gate 4 where the separation of the solids 2 from the fluid 3 takes place.

In the deformable state, the fluid medium 3 is in between the particles (elements), e.g. particle 2, separating them sufficiently for mutual movement. In this state, the solid particles form a deformable dispersion (or slurry).

If the fluid is removed from the interstitial spaces, the solid particles decrease their mutual separation and get into mutual contact. Their mutual movement is hindered and the deformability of the whole body decreases.

Figure 2A:
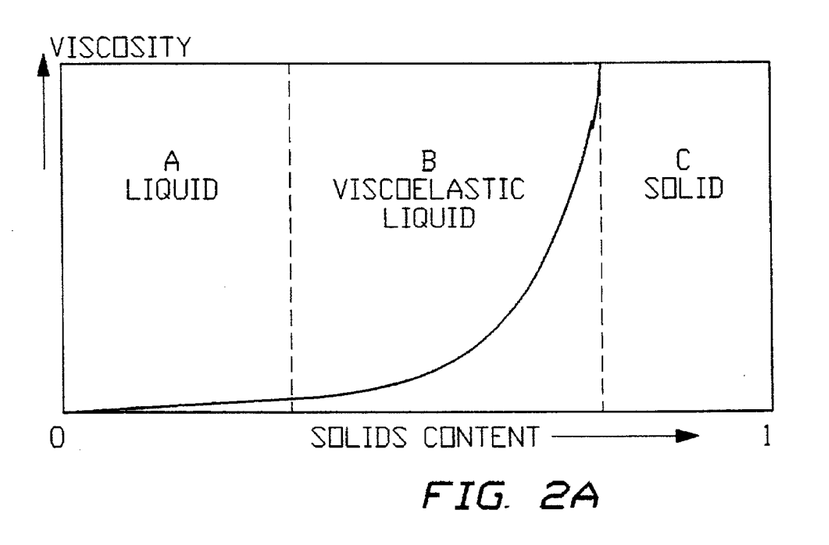
FIGS. 2A through 2D illustrate graphically the dependency of viscosity on solid content in solid/liquid dispersions (slurries)
Figure 2B:
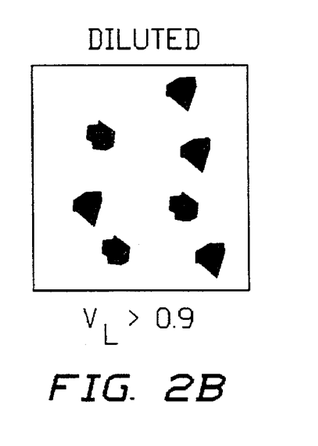
Figure 2C:
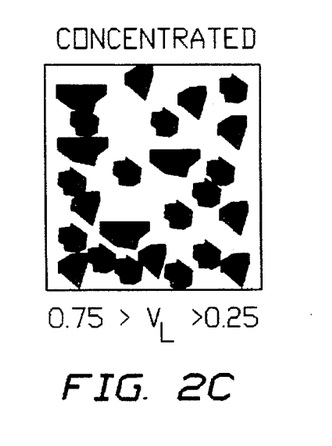

The principle of the operation can be further elucidated by the FIG. 2A where the graph in its upper part shows the very steep dependency of viscosity on solid content in solid/liquid dispersions (slurries). The lower part schematically depicts the diluted, concentrated and densely packed dispersions corresponding to the regions shown in FIGS. 2B, 2C and 2D of the graph, respectively. The region shown in FIG. 2B refers to diluted slurries with reduced viscosities proportional to solid volume fraction with factor 2.5 (Einstein-Simba equation). The region shown in FIG. 2C is where the solid-solid interaction starts to dominate rheology; the viscosity increases with solids content steeply. Because the direct contact between particles in intermission, the system is still deformable (forming a non-Newtonian fluid).

Figure 2D:
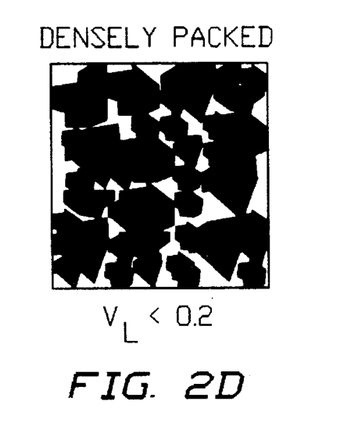

The region shown in FIG. 2D is a solid in which the interparticle interactions are direct, strong and long-lasting. Mutual mobility of particles ceases if the content of the interstitial fluid decreases below a certain value. The separating part of the fluid can transform the freely flowing dispersion into a densely packed slurry with solid-like behavior. (This is based on well known parts of colloid science, related, e.g., to clays, pastes, etc.)

Figure 3:
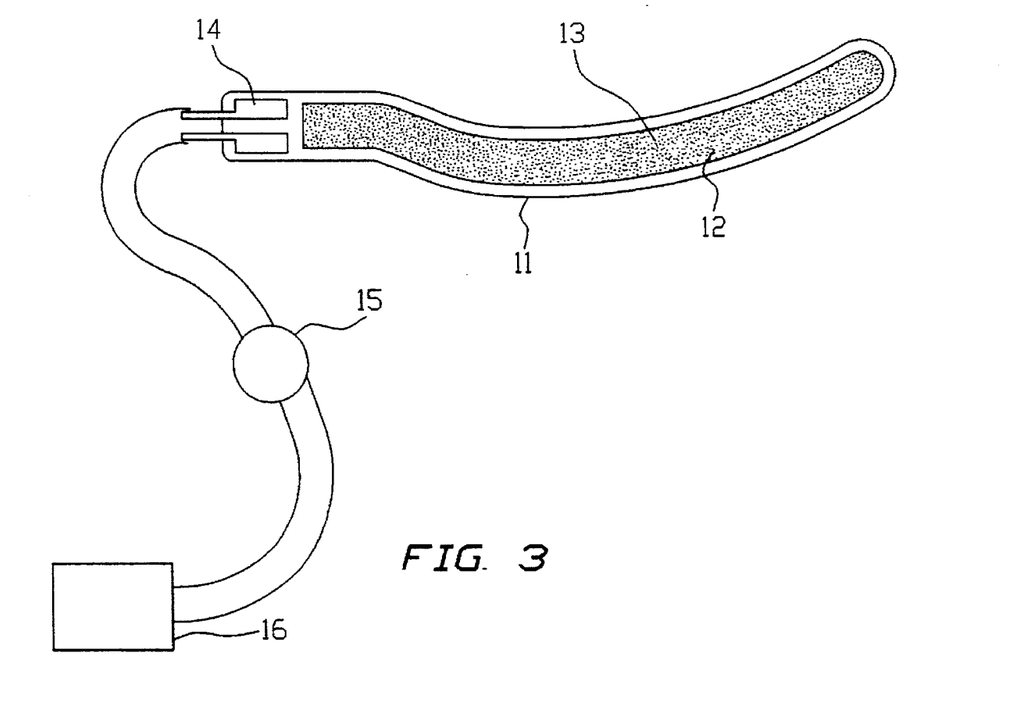
FIG. 3 shows a crossection view of another embodiment present invention device, a structure in which variable stiffness depends on a negative pressure change due to a vacuum application.

The interactive system according to our invention becomes more or less deformable due to the transition of the particles-fluid mixture between the states shown in FIGS. 2C and 2D and vice versa. This can be achieved by pumping the fluid from the intersticial spaces between the particles (e.g., by a mechanical pump, or by a vacuum) and returning it back when the deformability is needed again. FIG. 3 shows an alternative embodiment from that shown in FIG. 3 with an external container, with the stiffening element of this sort. There is the flexible wall 11 (e.g., a soft plastic poach), with solid particulate filler 12 (e.g., multitude of solid particles), and the fluid 13 in contact with the solid phase 12. The gate 14 is designed to separate the fluid 13 from the solid phase 12, and the pump 25 for transfer of the fluid 13 into the container 16 (a fluid receiver).

In this simple configuration, the fluid is transferred into the external container 16 so that the volume of the element changes between its deformable and rigid states. This may be a shortcoming for some applications. Therefore, in some preferred configurations, the fluid container is alternatively located within the wall, as shown in FIG. 1. The fluid is then redistributed within the device (i.e., within the interactive system) rather than being removed from it and re-introduced back. Since the fluid is redistributed within the element, the volume of the element is constant.

Figure 4A:
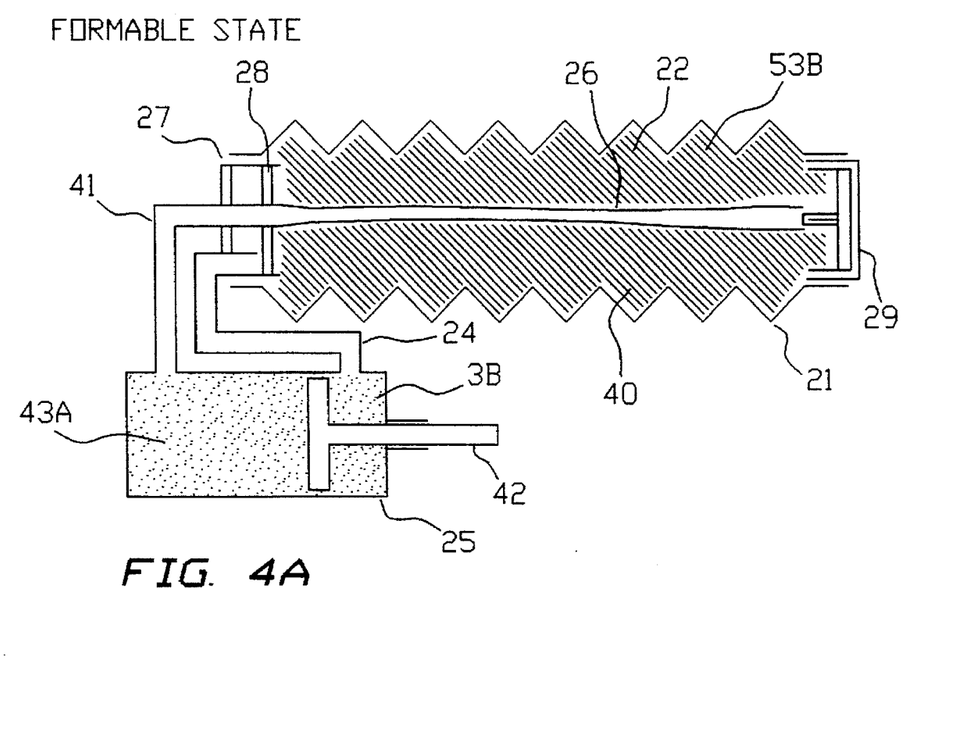
FIGS. 4A and 4B show a crossection view of another embodiment present invention device, a structure in which variable stiffness depends on pressure change due to a pumping action.

A simple representation of this preferred arrangement is in FIG. 4A wherein the numbers have the following meaning:

21—Bendable outside casing (e.g., a corrugated TEFLON tube);

29—Plastic plug enclosing one end of the casing 21;

27—Another plug, equipped with draining mesh 28, a draining outlet (the gate 24), and central outlet 41;

25—Fluid transfer device (e.g., a pump); 26—Plastic internal poach which is collapsed in the formable base state, but in the activated rigid state it is inflated by the fluid 43A. This poach can act as the fluid receiver; and, 40—Space filled with solid particles 22 dispersed in the fluid 53B.

In the bendable state (FIG. 4A), the poach 26 is empty and space 40 is filled with a relatively diluted, free-flowing slurry.

To stiffen the device and to retain its deformed shape, part of the fluid 53B is drained from space 40 by the pump 25 action (represented by movement of the plunger 42) while the poach 26 is inflated with the fluid 43A. The space 40 is now filled with the compacted slurry having a solid-state behavior, as represented by the Region C of FIG. 1.

The internal fluid receiver solves two problems of the interactive system:

a) The volume remains the same in the base and the activated states; and, b) The receivers inflation compresses the slurry against the more rigid outer wall and facilitates thus drainage as well as increasing the overall rigidity.

(In this arrangement, the fluid 43A in the receiver 26 does not need to be the very fluid 53A which is mixed with the solid particles 22. The fluid 43B can be drained into an outside receiver, while the internal poach 26 is filled by a substantially same volume of a different fluid, without exceeding the scope of the present invention.

The container receiving the drained fluid may not be necessarily a single poach. The "fluid receiver" can consist of a multitude of spaces, swellable particles or cells. It can be an advantage if also the fluid transfer device or mechanism is internal to the interactive system. The driving force for the fluid transfer can be derived from osmosis, electroosmosis or similar mechanisms. For instance, the fluid receptor can be a polymer particle capable to accept or reject the fluid depending on external conditions. There are numerous possibilities on how to realize the fluid transfer. For instance, the fluid container may be a particle absorbing the fluid in one temperature range and releasing the fluid in a different temperature range. It can also be a gel absorbing the liquid in the presence of an electric field and releasing the excess fluid once the filed ceased. It can also be a gel absorbing more liquid if illuminated than in absence of light.

The fluid can be either gas, or liquid. If the fluid is a gas, numerous possibilities exist. The most usual gas is obviously air. In that case, the "external fluid container" can be the atmosphere, and the device stiffens simply by pumping the air out and becomes deformable again by letting the air back into the device.

Another possible gas example is mixture of water, ammonia and carbon dioxide, which exists as solid ammonium bicarbonate at ambient temperature, but as a gas at moderately elevated temperatures.

Many more possibilities exist if the fluid is a liquid. The main advantage of the liquid over gas is its low compressibility allowing a steeper pressure change via a small volume change. Moreover, liquids affect the interaction between the solid surfaces in a very distinct way. Accordingly, the liquid can be selected according to its wetting capability with respect to the solid particles. It is often an advantage if the liquid does not wet the particle surface too well, and if the wetting angle is about 45 degrees or higher. The film separating the particles can then get destabilized even by a moderate pressure, and the particles can get into the direct interaction more easily. The liquid can be water, an aqueous solution, an organic liquid such a hydrocarbon, ester, alcohol, ether, ketone, etc. It can also be a mixture of two or more substances, or a solution of a polymer in a suitable solvent. The liquid receptor can be selected to suit the liquid in question.

One of the most useful liquids is water or an aqueous solution. Because of its high dielectric constant, water affects interaction between charged solid surfaces more than over liquids. If water is used as the liquid, the fluid receptor can be a hydrogel with a variable water-retention capability. There are hydrogels which change strongly their water-retention capability with temperature. If the water-absorption capability increases with temperature, the system stiffens with increasing temperature as the liquid is transferred from the interstitial spaces into the hydrogel. There are also hydrogels which deswell at a certain well defined temperature (LCDT for "lower critical dissolution temperature"). If such a hydrogel is used as the liquid receptor, the interactive system is more deformable at higher temperatures (above LCDT) while becoming stiffer below the LCDT.

There are also gels which increase their water content if exposed to an electric field. If such gels are used as a liquid receptor, electric field "stiffens" the interactive system as the liquid is transferred from the interstitial spaces into the gel. Contrary to the electro-rheological fluids, such a system can solidify to a truly solid mass, and it can do so by applying a field of much lower intensity.

There are also hydrogels containing chromophoric pendent groups, which become charged if illuminated by light of an appropriate wavelength. The illuminated hydrogel increases its swelling reversible. If such a hydrogel is used as the liquid receptor, the interactive system can be stiffened by the appropriate illumination.

The solid particles (or "elements") can be made of various materials: metal, ceramics, inorganic or organic salts, polymers, etc. The size of the particles varies in a very broad range, from about 0.1 microns to several millimeters.

If the elements have a relatively large.size (e.g., discs such as washers, beads, etc.), the fluid can be drained readily. However, their mutual interaction is limited due to a limited specific surface area.

Small particles of a powderous matter with large specific surface area can interact to form a stiff material with a good shape-retaining capability. However, the draining over a large distance posses a problem. If the particles are very small, the fluid should have a very low viscosity (e.g., a gas) and the fluid receptors should be well distributed therein (e.g., gel particles or fibers).

While the material of these particles is broadly optional, it should have a sufficient rigidity for a given purpose. Very rigid, hard particles (e.g. glass) can yield a very rigid interactive system in its activated state. If the particles are rubbery, even the solidified interactive system may be elastic.

Important criterion in the material selection is the capability of the mutual interaction between the particles. Advantageous are materials, which have both negative and positive surface charges, such as kaolinite. Preferred are materials with high coefficient of dry self-friction. The shape is preferably non-spherical with flat faces for secure locking (e.g., discs, plates, cubes, needles, hexagonal rods, irregular fragments, etc.)

The main considerations in the solid particle selection are the following:

a) Flexibility or formability in free (i.e., inactivated) state, (defined by apparent modulus of elasticity of the whole structure). It will be affected mainly by the filler geometry and size; and, b) Locked-in rigidity, defined by the apparent yield stress value of the device. For a given impulse value (e.g., for a certain value of the outside over-pressure), the rigidity will be affected mainly by the filler geometry, size, rigidity and mutual friction between individual elements or particles.

The selection of the filler and fluid can cover a very broad range of functional requirements.

In addition to the functional requirements, there are various safety requirements on the device: toxicity, flammability, and cost of used materials should be kept low. If the device is intended for a medical product, it should be sterilizable by various methods (e.g., by autoclave, ethylene oxide or by radiation).

The following Examples further illustrate the invention without defining or limiting its scope:

EXAMPLE 1

Plastic foil cuff has two adjacent chambers: the chamber A which is external, and chamber B which is internal (i.e. designed to be in contact with the limb). In the flacid state, the chamber A is deflated and chamber B is filled with an aqueous slurry of kaolinite crystals having average size about 0.1×1 mm. Concentration of the solids is 50% and pH=3.5. To stiffen the cuff, the aqueous solution is pulled from chamber A into a syringe and transformed into chamber B. While the excess of the liquid is in chamber A, the cuff can be readily shaped. Once the appropriate shape is achieved, the liquid excess is transferred from chamber A to chamber B. The negative pressure inside chamber A fixes the cuff in its shape and renders it undeformable. The return of the liquid excess into chamber A makes it shapable again.

This device can be used as a splice for temporary fixation of injured joints (e.g., elbow), and as an adjustable cast for bone fraction fixation.

EXAMPLE 2

A skiing boot is equipped with suitably located chambers with flexible polyurethane walls. One type of chambers (A) is filled with porous cross-linked polystyrene beads of an average diameter of about 10 microns. These chambers are located in areas where the variable flexibility of the boot is desirable.

Another type of chambers B is void of the filler. The chambers of this type are located in the areas of the boot where the change of the volume and of the pressure on the foot is desirable.

The chambers A and B are inter-connected via pump transferring air between them. (For instance, the air can be transferred between the chambers by a simple hand-operated pump, i.e. a flexible chamber with two one-way valves built into the boot). There is also a valve located in the transfer channels which can be operated from outside.

Once the operating fluid (i.e. air) is kept in both types of chambers under the ambient pressure, the whole boot is relatively flexible and allows for a comfortable put-on and for walking. Once the fluid is withdrawn from chamber A (which is now kept under a negative pressure) into the chamber A (which is kept under a positive pressure), the change in the state of the chambers A and B causes stiffening the boot and tighter fit for improved skiing control.

EXAMPLE 3

Figure 4B:
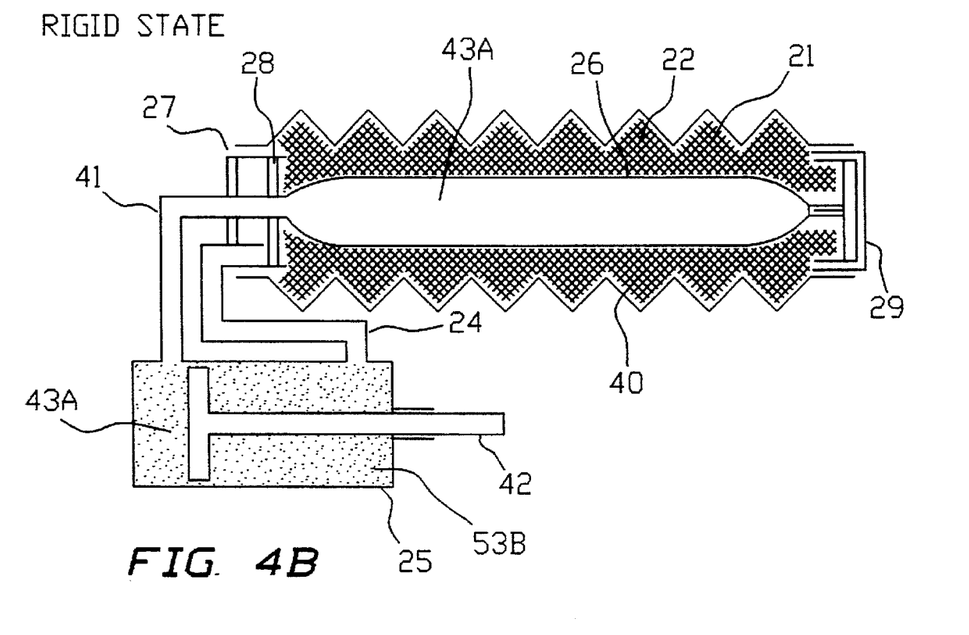

A strut with variable stiffness is shown in FIG. 4B. It is composed from the following components:

21—Bendable outside casing (a corrugated tube made of a rubber, TEFLON or similar polymeric material);

29—Plastic plug enclosing one end of the casing 21;

27—Another plug, equipped with draining mesh 28, a draining outlet (the gate 24), and central outlet 41;

25—Fluid transfer device (e.g. a piston pump as in FIG. 4A, or a peristatic pump, a gear pump or a membrane pump);

26—Plastic internal poach which is collapsed in the formable base state, but in the activated rigid state it is inflated by the fluid 43A. This poach can act as the fluid receiver.

40—Space filled with solid particles 22 dispersed in the fluid 53B.

The particles 22 may be discs (diameter 1 to 3 mm) made of poly (methylmetacrylate) polymer while the fluid 11 is ethylene glycol. The polymer is poorly wetted by the fluid, the wetting angle being larger than about 60°.

In the deformable state the device behaves as a deformable strut. In this state (FIG. 4A), the poach 26 is empty and space 40 is filled with a relatively diluted, free-flowing slurry of plastic discs and ethylene glycol. To stiffen the device, some part of the fluid 53B is drained from and transferred into the poach 26 by the pump 25. The space 40 is now filled with the compacted slurry having a solid-state behavior, and the device behaves as a solid element. The fluid 43A inflating the poach 26 is the same as the liquid 53B in this case.

EXAMPLE 4

A cross-linked gel is prepared by copolymerization of acrylamide with 10% of acrylic acid and 1% of N,N' methylene-bis-acrylamide between two pieces of a fine silver mesh coated with platinum. The gel is swelled in acetone-water mixture 1:1 by weight. The mesh pieces are connected to positive and negative poles, respectively, of a DC electrical source. If the electrical potential is applied, the gel shrinks by a factor of up to about 200 times, freeing the corresponding liquid amount. Once the mesh is disconnected from the electrical source, the gels swells again, reabsorbing the previously released liquid.

Figure 5A:
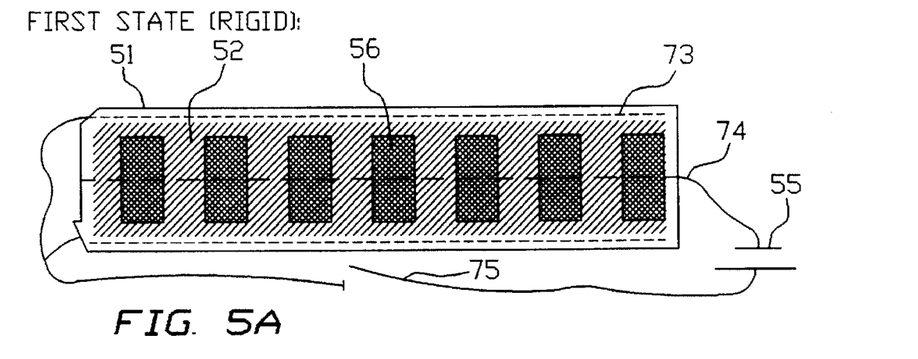
FIGS. 5A and 5B show a crossection view of another embodiment present invention device, a multilayer sandwich in structure which variable stiffness depends on an electrical impulse; and, FIGS. 6A and 6B a crossection view of another embodiment present invention device, a structure in which variable stiffness depends on temperature.
Figure 5B:
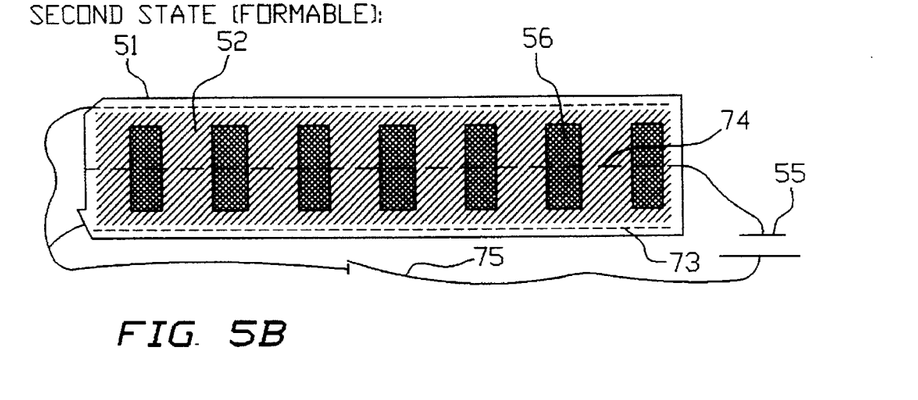

This element is used as the fluid transfer device and the fluid recipient at the same time. One of the possible configurations is in FIG. 5A and 5B. The device is a multi-layer sandwich formed by the following components:

51 outer casing;

52 kaolin slurry;

75 DC source (up to about 10 V);

56 Copolymer gel layer;

73 the metal mesh connected to the positive pole of the DC source 75;

74 the metal mesh connected to the negative pole of the DC source 75; and, 75 a switch closing the circuit.

In its basic rigid state, the circuit is disconnected by the switch 75 and the kaolin slurry 52 is dewatered, forming a compact, solid layer. The liquid is contained within the swollen gel layer 56. Once the switch 75 is connected and the electric potential is applied to the electrodes 73 and 74, the gel 56 deswells in the electric field, releasing the liquid into the layer 52. The diluted slurry becomes liquid, rendering the device deformable.

Disconnection of the circuit by the switch 75 causes re-absorption of the liquid into the gel 56, draining the slurry and turning the layer 52 solid.

The rate of the transition between the formable and the rigid states will be controlled by rate of the liquid diffusion from and into the gel 56. The gel forms with a large specific surface (fibers, fine particles, thin coatings) are preferred for a quick response.

This system can be utilized in various formats for devices which are stiff in the basis state, but which can be turned temporarily deformable (e.g. for insertion).

EXAMPLE 5

Figure 6A:
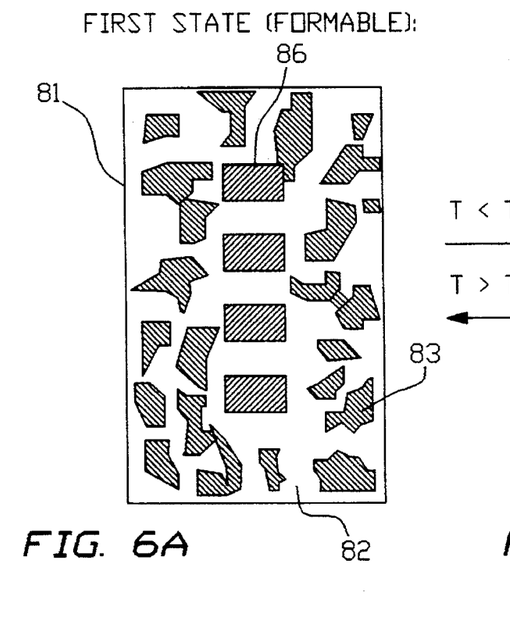
Figure 6B:
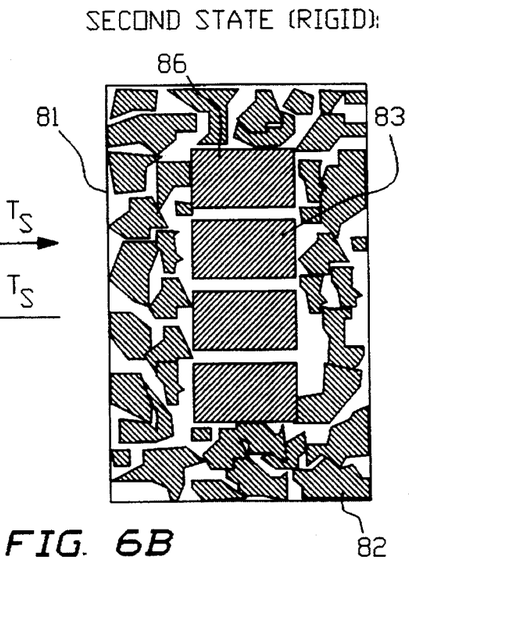

The device according to our invention which can be transformed between the formable and rigid states depending on temperature is schematically depicted in FIG. 6A and 6B wherein:

81 is the flexible outer casing poach;

82 is the aqueous liquid;

83 are solid particles; and, 86 are particles of hydrogel which deswells reversible if its temperature exceeds a certain temperature Ts.

The practical implementation of this arrangement can be done as follows:

Wet-ground mica particles 83 (particle size about 20 microns) is mixed with fine particles 86 of a hydrogel made by irradiation crosslinking of poly (methyl vinyl ether). This particular hydrogel swells with water at ambient temperature, but if heated over about 33 degrees Celsius, it deswells releasing excess of water. The mixture of the two types of particles and liquid 82 is filled into a soft plastic poach 81 and sealed. The filled poach 81 is now rigid at ambient temperatures as the water is contained in the hydrogel particles 86 and the mica particles 83 mixture is drained. If the poach is heated over 33 degrees Celsius (say, to body temperature), the hydrogel releases water which becomes available to form a flowable mica slurry. Therefore, the poach softens and becomes formable at elevated temperatures.

Other known hydrogels can release water at different temperatures. The selection of the hydrogel can be used to achieve various transition temperatures between stiff and formable states of the device.

The devices described in the previous examples can have form of various products. The examples of the products can be the following:

1) Catheters and similar insertable devices: for instance, a guide catheter with an end "hook" which is flexible for insertion and removal, but stiff while holding in place inside the artery.

2) Stents which keep ducts, vessels and body cavities open and which are to be inserted in flexible folded state, and unfolded and stiffened once in place.

3) Sphincters and valves: for instance, an implantable valve to cure incontinence.

4) Penile and similar implants: reversible stiffening by pressure on scrotum, or a pumping action, etc.

5) Targeted and on-demand drug delivery systems releasing a drug by an external impulse;

6) IOLs (insertable through small incision and/or having accommodative optics); and, 7) Engineering and similar applications: for example: fasteners, individually shapable chairs, skiing boots, adjustable fracture casts, individually shapable struts and protective packaging materials.

Obviously, numerous modifications and variations of the present invention are possible in light of the above teachings. It is therefore understood that in the scope of the appended claims, the invention may be practiced otherwise than as specifically described herein.

What is claimed is:

1. A device having a first state and a second state, said first state being at least semi-flexible and formable, and said second state being less flexible and less formable than said first state, said device being transformable from said first state to said second state, which comprises:

(a) a hollow body having at least partial flexibility and containing a plurality of particulate material therein;

(b) a plurality of particulate material permanently located within said hollow body;

(c) a fluid medium, having a first state wherein it is located in said hollow body and intermixed with said particulate material, and having a second state wherein it is located at least partly away from said particulate material, said first state and said second state corresponding to said first state and said second state of said device;

(d) fluid transfer means connected to said hollow body for removing said fluid medium from said particulate material of said hollow body to a fluid medium receptor and for returning said fluid medium thereto, thereby transforming said device from said first state to said second state and vice versa; and, (e) a fluid medium receptor located within said hollow body and connected to said fluid transfer means;

said fluid medium receptor being located within said hollow body and being surrounded by said particulate material.

2. The device of claim 1, wherein said fluid is a liquid.

3. The device of claim 2, wherein said fluid is an aqueous liquid.

4. The device of claim 1, wherein said fluid medium receptor is a closed container having a variable volume relative to the volume of said fluid medium received.

5. The device of claim 4, wherein said fluid transfer means is located within said hollow body.

6. The device of claim 4, wherein said fluid transfer means is located outside of said hollow body.

7. The device of claim 1, wherein said fluid transfer means is a controllable, variable liquid-absorption capacity transfer means formed of a gel material.

8. The device of claim 1, wherein said fluid transfer means is a gravity flow system and the flow of fluid medium to and from said hollow body is based on elevation differences between said fluid medium receptor and said hollow body.

9. The device of claim 1, wherein said fluid medium receptor is a closed container fillable with said fluid medium and having varying volume to compensate for the volume of said fluid medium removed from said hollow body such that the volume of said hollow body remains substantially constant.

10. The device of claim 1, wherein within said fluid medium receptor is a thin-walled poach of a polymeric material connected with the interior of said hollow body by said fluid transfer means.

11. The device of claim 1, wherein within said fluid medium receptor is said polymeric gel.

12. The device of claim 11, wherein within said gel is a hydrogel.

13. A device having a first state and a second state, said first state being at least semi-flexible and formable, and said second state being less flexible and less formable than said first state, said device being transformable from said first state to said second state, which comprises:

(a) a hollow body having at least partial flexibility and containing a plurality of particulate material therein;

(b) a plurality of particulate material permanently located within said hollow body;

(c) a fluid medium, having a first state wherein it is located in said hollow body and intermixed with said particulate material, and having a second state wherein it is located at least partly away from said particulate material, said first sate and said second state corresponding to said first state and said second state of said device;

(d) fluid transfer means connected to said hollow body for removing said fluid medium from said particulate material of said hollow body to a fluid medium receptor and for returning said fluid medium thereto, thereby transforming said device from said first state to said second state and vice versa; and, (e) a fluid medium receptor located within said hollow body and connected to said fluid transfer means;

said fluid medium receptor being an absorption material which is a gel polymer which reversibly imbibes said fluid medium to form a gel state.

14. The device of claim 13, wherein said gel is a hydrogel.

15. The device of claim 13, wherein the said gel polymer has a liquid-absorption capacity variable in a controllable manner in dependence on the value of at least one of the parameters selected from the group comprising temperature, pH of said fluid medium, water content in said fluid medium, intensity and polarity of electric field, intensity and polarity of magnetic field, intensity and frequency of electromagnetic field and intensity and wavelength of light.

16. The device of claim 13, wherein said fluid medium is an aqueous liquid.

17. The device of claim 13, wherein said fluid transfer means is a controllable, variable liquid-absorption capacity transfer means formed of a gel material.

18. A device having a first state and a second state, said first state being at least semi-flexible and formable, and said second state being less flexible and less formable than said first state, said device being transformable from said first state to said second state, which comprises:

(a) a hollow body having at least partial flexibility and containing a plurality of particulate material therein;

(b) a plurality of particulate material permanently located within said hollow body;

(c) a fluid medium, having a first state wherein it is located in said hollow body and intermixed with said particulate material, and having a second state wherein it is located at least partly away from said particulate material, said first state and said second state corresponding to said first state and said second state of said device;

(d) fluid transfer means connected to said hollow body for removing said fluid medium from said particulate material of said hollow body to a fluid medium receptor and for returning said fluid medium thereto, thereby transforming said device from said first state to said second state and vice versa; and, (e) a fluid medium receptor located within said hollow body and connected to said fluid transfer means;

said fluid medium receptor being composed of a multitude of independent cells for containing said fluid medium.

19. The device of claim 18, wherein the said multitude of independent cells are particles of a polymeric material capable of reversibly absorbing the said fluid medium.

20. The device of claim 18, wherein said particulate material is a homogeneous material of predetermined size range.

21. The device of claim 20, wherein said particulate material composed of particles of irregular, generally non-spherical shape.

22. The device of claim 20, wherein said particulate material is composed of particles having a shape selected from the group comprising spherical, cylindrical, disk-like, cubic, rectangular, hexagonal, lenticular, rhombic, polygonal and general multifaceted.

23. The device of claim 20, wherein said particulate material is an inorganic crystalline material.

24. The device of claim 20, wherein said particulate material is a material selected from a group comprising glass, ceramics, rigid plastics and elastomers.

25. The device of claim 20, wherein said particulate material is a multitude of regularly shaped polymeric bodies.

26. The device of claim 18, wherein said fluid medium is a gas.

27. The device of claim 26, wherein said gas is air.

28. The device of claim 26, wherein said gas comprises ammonia and carbon dioxide.

29. The device of claim 18, wherein said fluid medium is a liquid.

30. The device of claim 29, wherein said liquid is selected so that it wets poorly the said particulate material.

31. The device of claim 29, wherein said liquid comprises water.

32. The device of claim 18, wherein said hollow body is elastic and is expanded in its first state due to the fluid medium content.

33. The device of claim 32, wherein said fluid transfer means relies upon contraction of said hollow body for fluid medium removal to transform said hollow body to said second state and positive force to return said fluid medium to said hollow body to transform said hollow body to said first state.

34. The device of claim 18, wherein when said hollow body is in said first state, said fluid medium and said particulate material form a slurry.

35. The device of claim 34, wherein said hollow body is in said second state, individual particular material is in direct contact with one another to impart rigidity to said hollow body.

36. The device of claim 18, wherein said fluid transfer means is a means for imparting a pressure change to said hollow body to transfer fluid medium to and from said hollow body.

37. The device of claim 18, wherein said fluid transfer means is a means for imparting a temperature change.

38. The device of claim 18, wherein said fluid transfer means is a means for imparting a change in the said absorption capacity of the fluid medium by said fluid receptor due to a presence of electric field.

39. The device of claim 18, wherein said fluid transfer means is a means for imparting a change in the said absorption capacity of the fluid medium by said fluid receptor due to a presence of magnetic field.

40. The device of claim 18, wherein said fluid transfer means is a means for imparting a change in the said absorption capacity of the fluid medium by said fluid receptor due to an exposure to light.

41. The device of claim 18, wherein said fluid transfer means is a means for imparting a change in the said absorption capacity of the fluid medium by said fluid receptor due to a temperature change.

* * * * *